US 6,450,007 B1

(12) United States Patent
O'Connor

(10) Patent No.: US 6,450,007 B1
(45) Date of Patent: Sep. 17, 2002

(54) ROBUST SINGLE-CHIP HYDROGEN SENSOR

(75) Inventor: James M. O'Connor, Ellicott City, MD (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 09/729,147

(22) Filed: Dec. 1, 2000

Related U.S. Application Data

(60) Provisional application No. 60/168,241, filed on Dec. 1, 1999.

(51) Int. Cl.[7] .............................. H01C 7/00; H01L 7/00; H01L 29/66; G01N 21/41; G01N 31/06
(52) U.S. Cl. ...................... 73/23.2; 73/31.05; 73/23.31; 422/90; 422/94; 338/34
(58) Field of Search ............................... 73/23.2, 31.05, 73/31.06; 422/90, 94; 338/34

(56) References Cited

U.S. PATENT DOCUMENTS

| | | | | |
|---|---|---|---|---|
| 4,977,658 A | * | 12/1990 | Awano et al. | 29/25.01 |
| 5,279,795 A | | 1/1994 | Hughes et al. | 422/98 |
| 5,367,283 A | * | 11/1994 | Lauf et al. | 338/34 |
| 5,493,897 A | * | 2/1996 | Nomura et al. | 73/23.2 |
| 5,668,301 A | * | 9/1997 | Hunter | 73/23.2 |
| 5,698,771 A | * | 12/1997 | Shields, et al. | 73/31.05 |
| 6,006,582 A | * | 12/1999 | Bhandari et al. | 73/23.2 |
| 6,041,643 A | * | 3/2000 | Stokes et al. | 73/31.06 |
| 6,114,943 A | * | 9/2000 | Lauf | 338/34 |
| 6,155,099 A | * | 12/2000 | Kobayashi et al. | 73/31.05 |
| 6,182,500 B1 | * | 2/2001 | Stokes et al. | 73/31.06 |

OTHER PUBLICATIONS

Author: Yang–Tse Cheng, Yang Li, Dan Lisi, W. M. Wang, Title: "Preparation And Characterization of Pd/Ni Thin Films For Hydrogren Sensing", in the Sensors and Actuators B 30 (1996) 11–16, Article Received Sep. 5, 1994; revised Jan. 17, 1995; accepted Jan. 20, 1995, pp. 11–16.

Author: R. C. Hughes, W. K. Schubert, Title: "Thin Films Of Pd/Ni Alloys For Detection Of High Hydrogen Concentrations", in the J. Appl Phys. 71 (1), Jan. 1, 1992, Received May 23, 1991, accepted for publication Sep. 27, 1991, pp. 542–544.

Author: R. C. Hughes, T. J. Boyle, T. J. Gardner, C. J. Brinker and Ross Thomas, Title: "Thin Film Porous Membranes For Catalytic Sensors", in the Digest of the 1997 International Conference on Solid State Sensors and Actuators, Transducers '97, Pages: All Pages.

* cited by examiner

Primary Examiner—Hezron Williams
Assistant Examiner—David J. Wiggins
(74) Attorney, Agent, or Firm—McDonnell, Boehnen, Hulbert & Berghoff

(57) ABSTRACT

A robust single-chip hydrogen sensor and a method for fabricating such a sensor. By adding an adhesion-promoting layer between the body of a sensor and an on-chip hydrogen-exposed electrically-resistive hydrogen-sensing element, device yields are improved when compared to directly applying the electrically-resistive hydrogen-sensing elements to the sensor body. The resistance of the sensing element is indicative of the hydrogen in the medium surrounding the sensor. According to a preferred embodiment of the present invention, the adhesion-promoting layer is a chromium (Cr) adhesion layer, and the hydrogen-exposed electrically resistive hydrogen sensing element is a PdNi alloy.

19 Claims, 5 Drawing Sheets

ROBUST SINGLE-CHIP HYDROGEN SENSOR

PRIORITY

This application claims priority to U.S. Provisional Patent Application No. 60/168,241, titled "Manufacturable Single-Chip Hydrogen Sensor," filed on Dec. 1, 1999, and naming James M. O'Connor as an inventor.

FIELD

The present invention is related to hydrogen sensors, and more particularly, to a robust single-chip hydrogen sensor and method for manufacturing the same.

BACKGROUND

During the early 1990s, Sandia National Laboratory developed a single-chip hydrogen sensor that utilized Palladium-Nickel (PdNi) metal films as hydrogen gas sensors. U.S. Pat. No. 5,279,795, naming Robert C. Hughes and W. Kent Schubert as inventors, assigned to the United States as represented by the U.S. Department of Energy, describes such a sensor and is incorporated by reference herein.

One of the key benefits of the sensor described in the '795 patent is its ability to detect a dynamic range of hydrogen concentrations over at least six orders of magnitude. Prior solutions to the problem of detecting hydrogen concentrations had been generally limited to detecting low concentrations of hydrogen. These solutions include such technologies as metal-insulator-semiconductor (MIS) or metal-oxide-semiconductor (MOS) capacitors and field-effect-transistors (FET), as well as palladium-gated diodes.

The hydrogen sensor described in the '795 patent was a notable advance in hydrogen-sensing technology. It was, however, primarily limited to an experimental laboratory environment due to the difficulties encountered in manufacturing such a sensor.

In typical silicon fabrication facilities, metal films are first blanket-deposited across the entire wafer, and are subsequently patterned by an etch process. However, conventional etchants for PdNi also attack aluminum, which is present on the wafer surface as an interconnect metal before the PdNi film is deposited. Patterning the PDNI by etching would also attack the unprotected aluminum, destroying the sensor. Even some non-conventional semiconductor fabrication techniques involving the use of a photoresistive material applied before the PdNi in a "lift-off" process have produced very low yields in tests performed by the assignee of the present invention. Low yields in the production of semiconductor devices typically translates to difficulties in producing a commercializable product.

It would be desirable to provide a robust single-chip hydrogen sensor that is capable of sensing hydrogen concentrations over a broad range, such as from less than 1% to approximately 100% concentrations.

It would also be desirable for such a sensor to be efficiently manufacturable, so that costs are reduced and the sensor is producible in high enough yields to enable commercialization.

It would be desirable for such a sensor to provide measurement results that approximate or improve on the results from previous hydrogen sensors.

It would additionally be desirable to minimize sensor drift and to improve device-to-device and wafer-to-wafer repeatability.

SUMMARY

In accordance with an illustrative embodiment of the present invention, some of the problems associated with manufacturing a robust hydrogen sensor are addressed.

Various embodiments of the invention provide a robust single-chip hydrogen sensor and a method for fabricating such a sensor. By adding an adhesion-promoting layer between the body of a sensor and an on-chip resistive hydrogen-sensing element, device yields are improved when compared to directly applying the resistive hydrogen-sensing elements to the sensor body.

According to a preferred embodiment of the present invention, the adhesion-promoting layer is a chromium (Cr) adhesion layer, and the resistive hydrogen-sensing element is a PdNi alloy.

BRIEF DESCRIPTION OF THE DRAWINGS

Presently preferred embodiments of the invention are described below in conjunction with the appended drawing figures, wherein like reference numerals refer to like elements in the various figures, and wherein.

DETAILED DESCRIPTION

Figure 1:
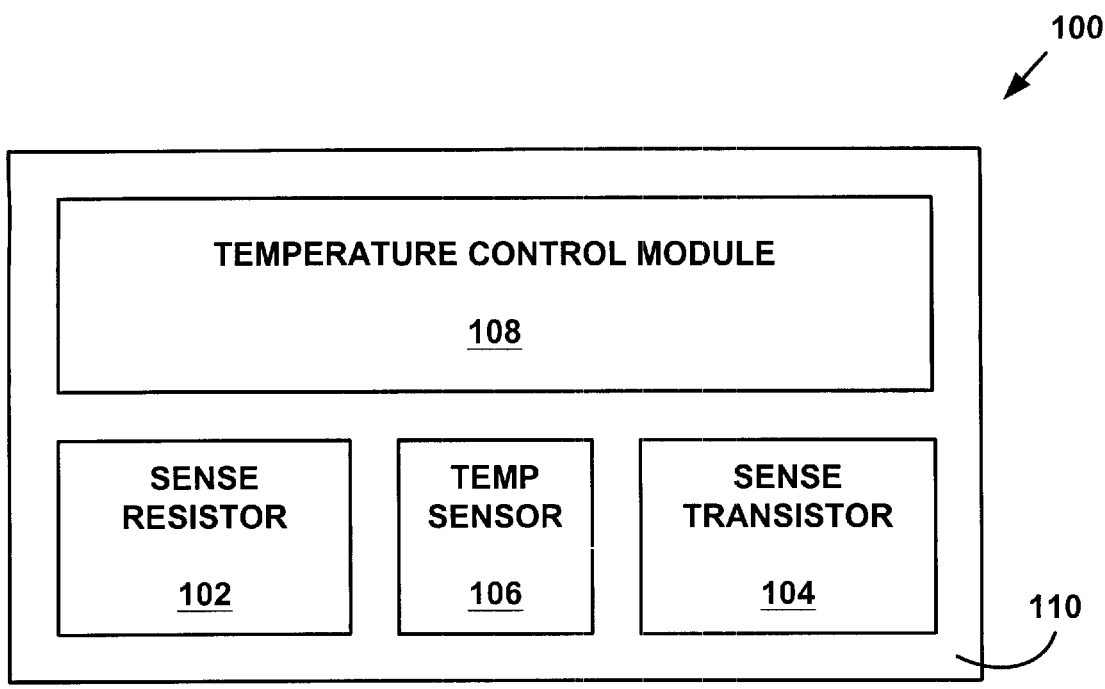
FIG. 1 is a simplified block diagram illustrating a top view of a robust single-chip hydrogen sensor according to an embodiment of the present invention.
Figure 3:
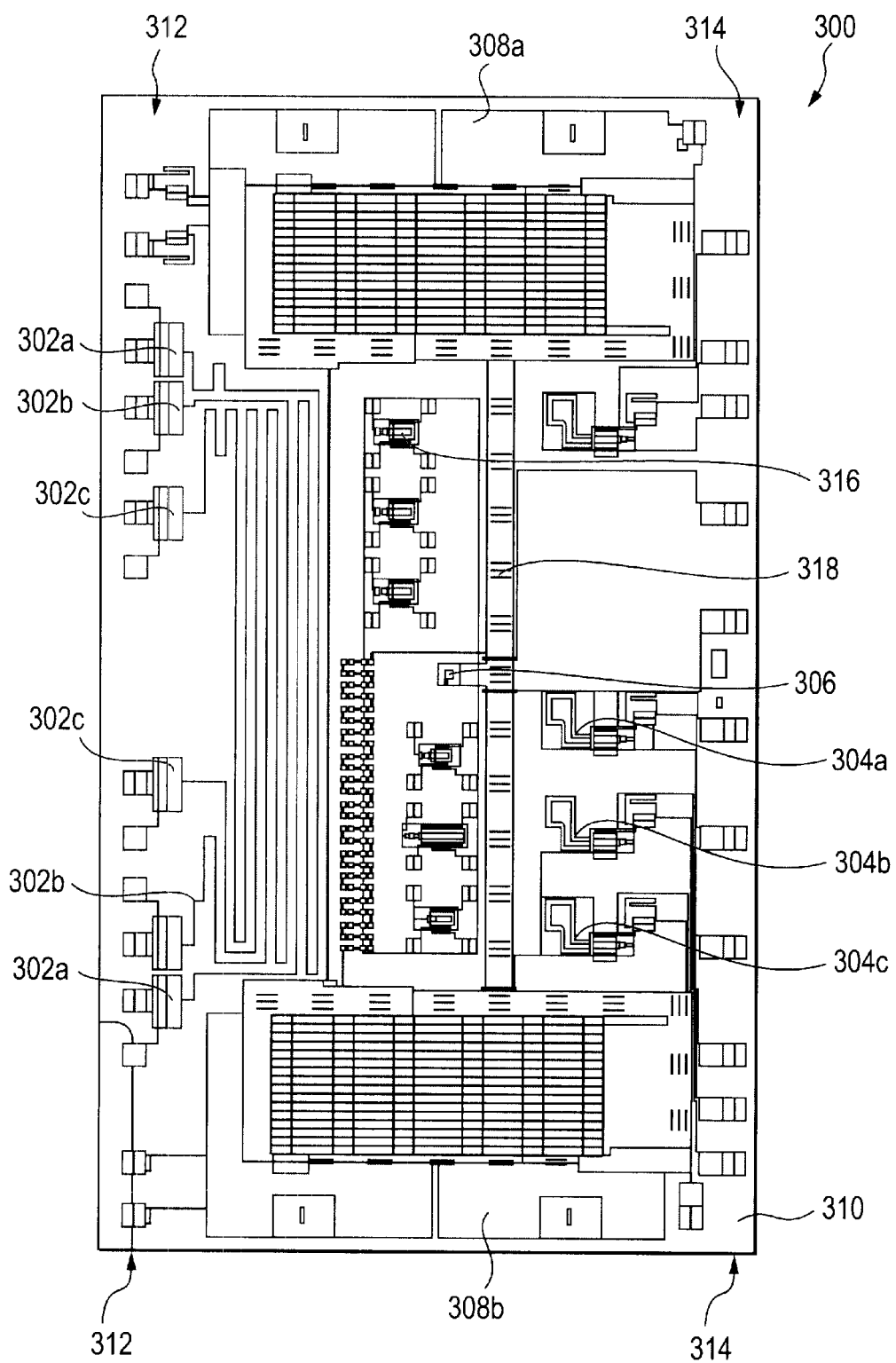
FIG. 3 is a block diagram illustrating a top view of a robust single-chip hydrogen sensor device according to a preferred embodiment of the present invention.

FIG. 1 is a simplified block diagram illustrating a top view of a robust single-chip hydrogen sensor in accordance with an embodiment of the present invention. The sensor 100 includes at least one sense resistor 102, at least one sense transistor 104, at least one temperature sensor 106, and at least one temperature control module 108 located in or on a substrate 110. External circuitry (not shown) may be included to assist in precisely regulating the temperature of the chip 100 using the temperature sensor 106 and the temperature control module 108. Similarly, the same external circuitry, or other external circuitry, may be used to obtain outputs from the sense resistor 102 and/or the sense transistor 104. For purposes of illustration, no connections are shown, and no external circuitry is shown in FIG. 1. Connections are likely to exist between the resistor 102, the sense transistor 104, the temperature sensor 106, the temperature control module 108, and/or any external circuitry. Further details on potential connections are shown in FIG. 3, described in further detail below. Also not shown is an underlying, non-conductive layer that may be used to isolate the sense resistor 102, the sense transistor 104, the temperature sensor 106, and/or the temperature control module 108 from the substrate 110. As used throughout this description, the term "non-conductive" is intended to describe conductive characteristics when compared to a conductive material, such as aluminum, or a semiconductive material, such as silicon. "Non-conductive" is not intended to imply an actual inability to. conduct electricity regardless of applied conditions.

The substrate 110 preferably is a bulk silicon substrate. Silicon enables the use of many common silicon semiconductor processing techniques, such as masks, implants, etchings, dopings, and others.

The temperature control module 108 preferably includes one or more heater Field-Effect-Transistors (FETs) or other heating devices formed in or on the substrate 110. One or more cooling mechanisms may additionally or alternatively be included as part of the temperature control module 108. The temperature control module 108 adjusts the temperature of the sensor 100 in response to temperature measurements received from the temperature sensor 106 or associated external circuitry.

The temperature sensor 106 is preferably a temperature sensing diode formed in or on the substrate 110. Other methods for sensing temperature may also be used.

The sense transistor 104 is used to sense hydrogen concentration levels in an environment in which the sensor 100 is placed. The sense transistor 104 is preferably a PdNi-gate sense transistor that is fabricated in or on the substrate 110. Other types of sense transistors may also be used. The sense transistor 104 may utilize Metal-Oxide-Semiconductor (MOS) or Metal-Insulator-Semiconductor (MIS) technology. In an alternative embodiment, the sense transistor 104 may be a sense capacitor, such as an MOS capacitor. (In such a case, alternating current measurement techniques may need to be employed.) The sense transistor 104 senses hydrogen concentration levels ranging from a first minimum concentration to a first maximum concentration. Typical values for the first minimum concentration and first maximum concentration are one part per million (ppm) and 1,000 ppm, respectively. Other minimum and maximum concentrations may also be possible for the sense transistor 104.

The sense resistor 102 is preferably a PdNi film arrayed in a serpentine pattern fabricated in or on the sensor 100. The resistance of the sense resistor 102 changes in the presence of hydrogen, enabling detection of hydrogen concentration in a particular environment. The sense resistor 102 is preferably operable to sense hydrogen levels ranging from a second minimum concentration to a second maximum concentration. Exemplary values for the second minimum concentration and second maximum concentration are 100 ppm and 1,000,000 ppm, respectively. Other minimums and maximums may also be possible.

Figure 2A:
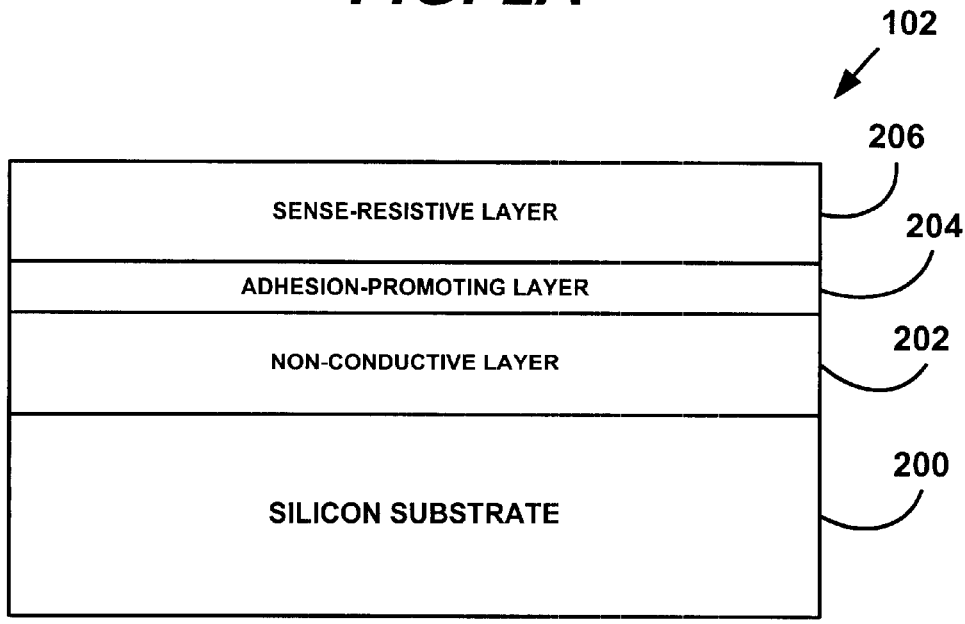
FIG. 2A is a conceptual diagram illustrating a side view of a sense resistor according to an embodiment of the present invention.

FIG. 2A is a simplified conceptual diagram illustrating a side view of the sense resistor 102 according to an embodiment of the present invention. FIG. 2A is not necessarily to scale. The sense resistor 102 is fabricated on or in a portion of a silicon substrate 200, or on another layer above the silicon substrate 200. A non-conductive layer 202 is formed on the silicon substrate (or on another layer, such as a conductive layer, above the silicon substrate). The non-conductive layer 202 may, for example, be a silicon nitride or oxide layer. An adhesion-promoting layer 204 is formed on the non-conductive layer 202 (or another layer, such as a conductive interconnect layer, for example). The adhesion-promoting layer 204 is preferably a thin (approximately 50 Angstroms thick) layer of chromium (Cr). A sense-resistive layer 206, such as a PdNi film, is then deposited on the adhesion-promoting layer 204 and/or on one or more other layers. Other materials besides PdNi may be used, such as various palladium silicides and polymeric sensing elements. References to layers other than the silicon substrate 200, the non-conductive layer 202, the adhesion-promoting layer 204, and the sense-resistive layer 206 are intended to accommodate the various interconnections, contacts, and other semiconductor structures that may exist on the sensor 100.

The use of the adhesion-promoting layer 204 assists in improving adhesion of the sense-resistive layer 206 to another underlying layer. This results in a substantial improvement in device yield, since the sense-resistive portions that are intended to become part of the sense resistor 102 do not peel off during the lift-off process described in the Background section herein. Similarly, peel-off is prevented during subsequent die- sawing steps that are likely to be performed in a commercial manufacturing setting. The assignee of the present invention found device yields to improve from approximately 10% to approximately 90%. Another advantage realizable by the use of the adhesion-promoting layer 204 may include reduced drift and hysteresis when the sensor 100 is being used to detect hydrogen. Improved device-to-device and wafer-to-wafer repeatability is also possible. The latter advantages may be due to the improved ability to fine-tune the resulting structure and coverage of the sense-resistive layer 206.

Figure 2B:
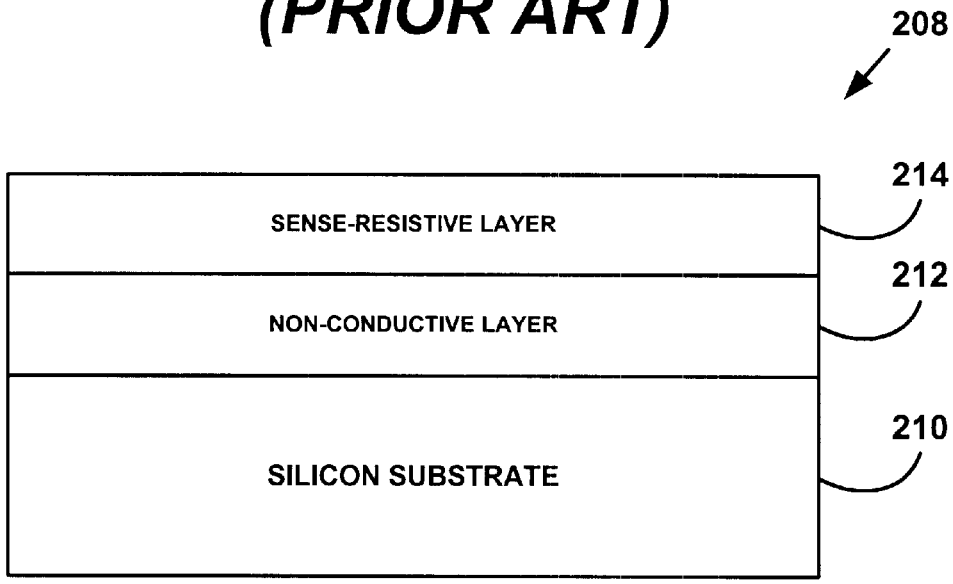
FIG. 2B is a conceptual diagram illustrating a side view of a previous sense resistor.

FIG. 2B is a simplified conceptual diagram illustrating a side view of a previous sense resistor 208. The previous sense resistor 208 consists of a non-conductive layer 212 deposited on a silicon substrate 210. A sense-resistive layer 214 is then deposited on the non-conductive layer 212. The previous sense resistor 208 does not include the adhesion-promoting layer between the sense-resistive layer 214 and the non-conductive layer 212. As a result, undesired peel-off may occur during processing or die-sawing, leading to lower yields.

Operation of the sensor 100 will now be briefly described. The temperature sensor 106 and temperature control module 108 are used to regulate the operating temperature of the sensor 100 when sensing hydrogen. The temperature of the sensor 100 may, for example, be held at a constant sense temperature. The temperature sensor 106 and temperature control module 108 may also be used to purge hydrogen and/or other gases, etc. after measurements are taken, by heating the chip to a purge temperature. In the preferred embodiment, the temperature control module 108 heats the chip to approximately 80 degrees Celsius, as measured at the temperature sensor 106. The purge temperature is preferably approximately 100 degrees Celsius. One or more feedback loops may be used to assist in accurately regulating the temperature using the temperature sensor 106 and the temperature control module 108. Such feedback loop(s) may be included in external circuitry, for example. When the sensor 100 is in a hydrogen-sensing mode, then the sense resistor 102 and the sense transistor 104 preferably sense hydrogen levels at overlapping ranges. This enables the combination of the sense resistor 102 and the sense transistor 104 to provide measurements of hydrogen concentration over a larger range than a single sense element might otherwise provide. The determination as to when to purge may be made by examining measurement outputs from the sense resistor 102 and/or the sense transistor 104. In the case of the sense resistor 102, the measurement output may be a particular resistance corresponding to the concentration of hydrogen gas in the environment of the sensor 100. Such a determination may be made by external circuitry and may be used to control the temperature control module 108.

FIG. 3 is a block diagram illustrating a top view of a single-chip hydrogen-sensing device 300, according to a preferred embodiment of the present invention. The device 300 includes a first sense resistor 302a, a second sense resistor 302b, and a third sense resistor 302c, to sense hydrogen concentrations at approximate first minimum concentrations and approximate first maximum concentrations. A first sense transistor 304a, a second sense transistor 304b, and a third sense transistor 304c may be used to sense hydrogen levels at second minimum concentrations and second maximum concentrations. A temperature sensing diode 306 is used to determine the temperature of the device 300. A first heater Field Effect Transistor (FET) 308a and a second heater FET 308b are used to control the temperature of the device 300, so that the approximate temperature is 80 degrees Celsius during a hydrogen-sensing period and approximately 100 degrees Celsius during a purge period. The temperature sensing diode 306 and the heater FETs 308a–b are used in conjunction with external circuitry (not shown) to provide temperature regulation. The sense resistors 302a–c, the sense transistors 304a–c, the temperature sensing diode 306, and the heater FETs 308a–b are located in and/or on a bulk semiconductor substrate 310. Additional layers may be present on the substrate 310, and are not shown in FIG. 3. For example, conductive and/or non-conductive layers may be deposited on one or more portions of the substrate 310. A series of left-side contacts 312 extend generally down the left side of the device and may be used to provide power, to receive measurements, and to control device operation. Similarly, right-side contacts 314 may be used to provide these same operations. In addition, the left-side contacts 312 and the right-side contacts 314 may be used for other functions, such as for testing the device 300. Special test elements, such as the test element 36 (and others resembling test element 31), may be located in or on the device 300 to enable verification that the device 300 is operating properly. An interconnection network 318 connects various components within the device 300. Most of the unreferenced components shown in FIG. 3 are test elements.

The device 300 includes multiple sense resistors 302a–c, sense transistors 304a–c, and heater FETs 308a–b in order to provide redundancy. This enables the device 300 to operate in case one of the sensing mechanisms fails, and also enables improved accuracy due to more than one sensing element providing measurements and the ability to cross-check measurements. Other quantities of components within the device 300 may also be used without departing from the scope of the present invention.

The sense resistors 302a–c are preferably constructed as is shown in FIG. 2A. In particular, the sense resistors 302a–c consist of a thin (approximately 50 Angstroms thick) adhesion-promoting layer 204 deposited on a non-conductive layer 202 (such as a silicon nitride or oxide), which is located on a conductive layer (such as aluminum) or on the silicon substrate 310. The adhesion-promoting layer preferably is a chromium thin film. Other adhesion-promoting materials may also be used, and are intended to be within the scope of various embodiments of the invention. The adhesion-promoting layer (such as the chromium film) is preferably of a thickness in the range of 25 Angstroms to 100 Angstroms. The sense-resistive layer 206 is preferably an alloy that resists the formation of a hydride phase of a catalytic metal contained in the alloy. The preferred alloy is a nickel and palladium alloy (PdNi). For example, an alloy of about 8% to 20% (by atom percentage) nickel (with the balance being palladium) may be used. Other alloy compositions may also be used. The adhesion-promoting layer 204 helps to bond the sense-resistive layer 206 to the non-conductive layer 202, such as by forming an oxide.

In a preferred embodiment, PdNi is used as the hydrogen-sensing material. PdNi is not typically used in semiconductor manufacturing. In typical silicon fabrication facilities, metal films are first blanket-deposited across the entire wafer and are subsequently patterned by an etch process. Conventional etchants for PdNi, however, also attack various interconnect metals, such as aluminum. Because the preferred embodiment of the device 300 utilizes aluminum as an interconnect metal, use of a conventional etchant for PdNi would also attack the aluminum before the PdNi film is deposited. This would likely destroy the sensor. Thus, instead of using blanket-deposition and etching for patterning the PdNi layer, a lift-off patterning technique is used.

A lift-off patterning technique, according to the present invention, may be utilized after traditional semiconductor processing of the device 300 has been completed. A layer of photoresist (or other photo-sensitive polymer) is first coated over the entire wafer surface. A pattern is exposed in this layer 202, corresponding to the locations in which the sensing element (i.e., sense resistor 302a–c) will reside. The photoresist is then removed in the areas where the sensing element will reside, leaving a photoresist coating over the remainder of the wafer. The wafer is then placed in a vacuum chamber and evacuated. Once under vacuum, a thin layer 204 of chromium (approximately 50 Angstroms thick) is deposited. Then, a layer of PdNi 206 of suitable thickness is deposited. The remaining photoresist layer is removed, lifting off in the process the unwanted Cr/PdNi film and leaving behind the serpentine structure shown for the sense resistors 302a–c in FIG. 3.

Figure 4:
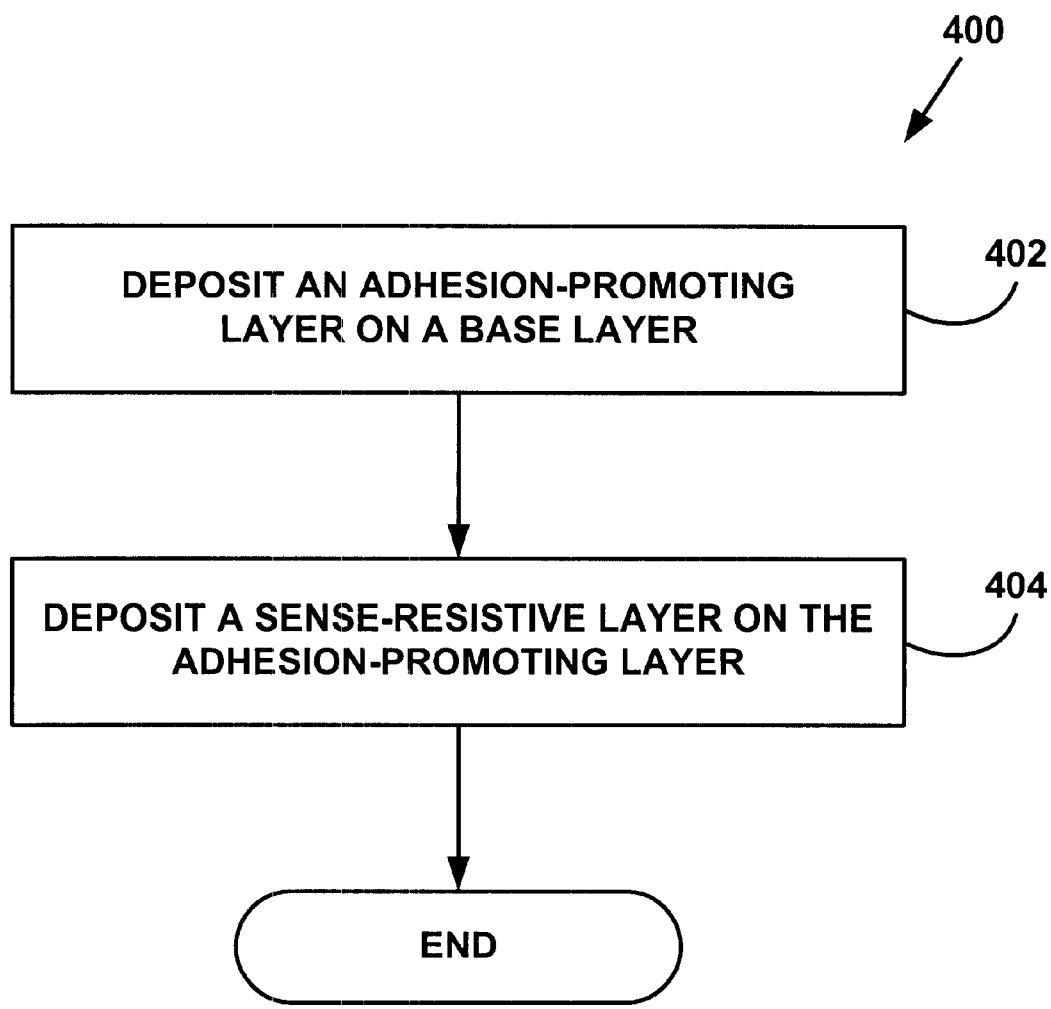
FIG. 4 is a flow diagram illustrating a method for manufacturing a robust single-chip hydrogen sensor according to an embodiment of the present invention.

FIG. 4 is a flow diagram illustrating a method 400 for fabricating a single-chip hydrogen sensor, according to an embodiment of the present invention. In step 402, an adhesion-promoting layer is deposited on a base layer. In step 404, a sense-resistive layer is deposited on the adhesion-promoting layer. In a preferred embodiment, the base layer includes at least a semiconductor substrate, and may additionally include a conductive layer and/or a non-conductive layer. The adhesion-promoting layer is preferably a thin film layer (less than approximately 100 Angstroms thick) of chromium (Cr). The sense-resistive layer is preferably a thin film layer (several hundred Angstroms to several thousand Angstroms thick) of palladium nickel (PdNi). Other thicknesses and compositions of the adhesion-promoting layer and the sense-resistive layer may also be used.

Figure 5:
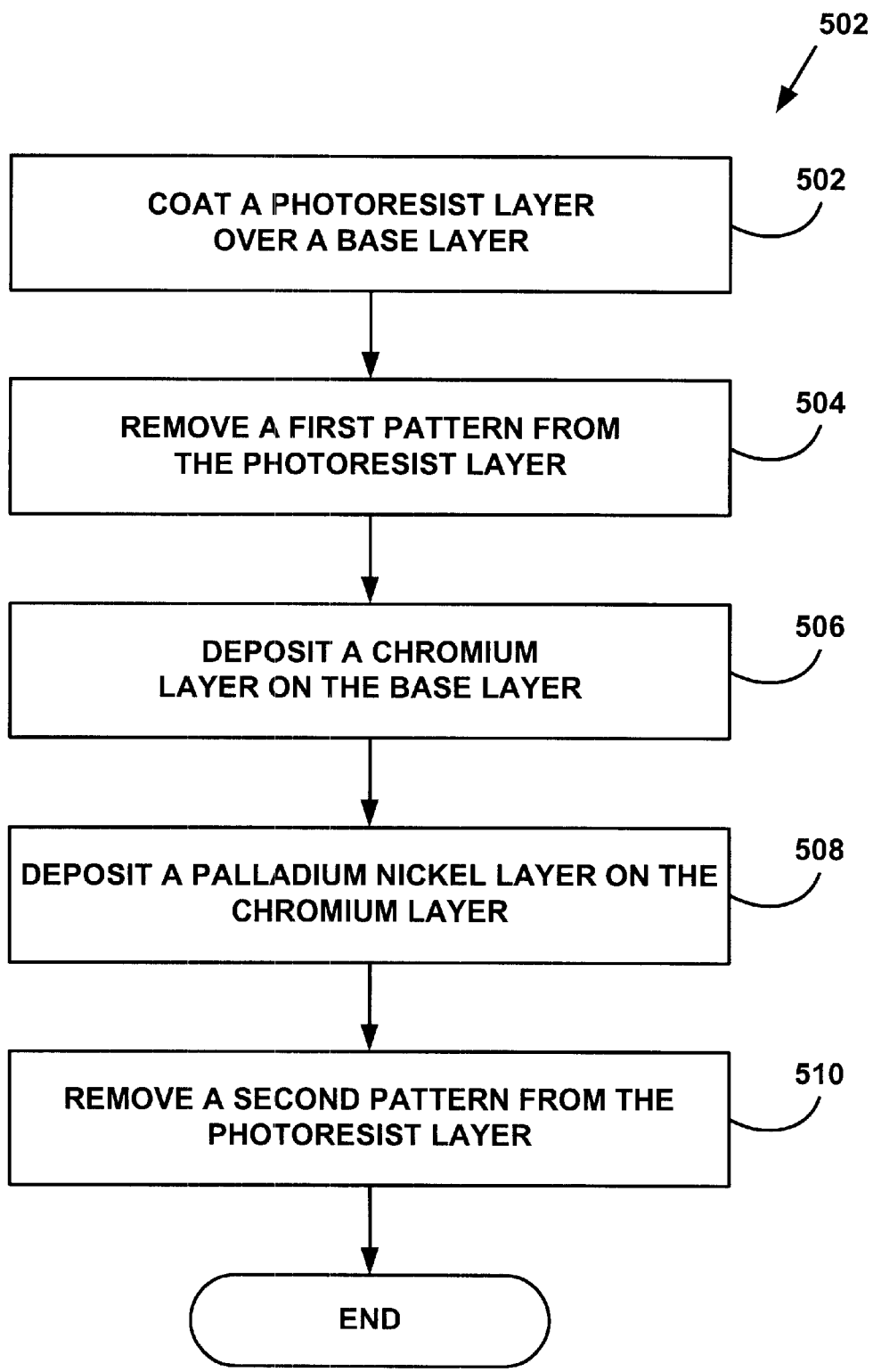
FIG. 5 is a flow diagram illustrating a method for fabricating a single-chip hydrogen sensor, according to a preferred embodiment of the present invention.

FIG. 5 is a flow diagram illustrating a method 500 for fabricating a single-chip hydrogen sensor, according to a preferred embodiment of the present invention. In step 502, a photoresist layer (or other photosensitive polymer layer) is coated over a base layer. In step 504, a first pattern (corresponding to the desired layout of the sense resistor) is removed from the photoresist layer, such as by applying light to the various portions photoresist layer and dissolving the exposed areas. In step 506, a thin film layer (approximately 50 Angstroms thick) of chromium is deposited. In step 508, a thin film layer (approximately several hundred Angstroms thick) layer of palladium nickel is deposited. In step 510, a second pattern (corresponding to the areas in which PdNi is to absent) is removed from the photoresist layer, "lifting off" the unwanted Cr/PdNi film and leaving behind the desired structure of the sense resistor. In a preferred embodiment, the base layer includes at least a semiconductor substrate, and may additionally include a conductive layer and/or a non-conductive layer. The Cr/PdNi film is preferably deposited by plating.

The chromium layer (or other adhesion-promoting layer) provides several advantages, as described above with reference to FIG. 2A. The adhesion-promoting properties of the chromium layer overcome many difficulties caused by the presence of photoresist on the wafer before the PdNi deposition. The presence of a photoresist layer precludes using many typical aggressive pre-cleaning steps, such as ion bombardment, sputter pre-clean techniques, and solvent cleaning techniques. As a result, the area where the PdNi is to be deposited is not as clean as it might otherwise be, adversely affecting film adhesion. Furthermore, if a wet chemical soak is used to dissolve the photoresist layer during lift-off, film adhesion may be even more adversely affected. The chromium layer is intended to address these adhesion problems.

TABLE 1 illustrates process steps that may be used to produce the single-chip hydrogen-sensing device 300, according to a preferred embodiment of the present invention. The steps are preferably performed in order, from top-to-bottom, starting with the left column. The abbreviations correspond primarily to semiconductor processing steps. Such abbreviations should be readily apparent to those having skill in the relevant technology field. It should be noted that the last six steps in the third column describe an embodiment of the method described herein, including depositing an adhesion-promoting layer (Cr) before depositing a sense-resistive layer (PdNi).

TABLE 1

| Phos Implant | spacer ox | BPSG |
|---|---|---|
| initial ox | n+ mask | BPSG reflow |
| diff mask | n+ imp | contact mask |
| diff etch | s/d implant | contact etch |
| p-well mask | poly re-ox | metal 1 dep |
| p-well imp | p+ mask | metal 1 mask |
| chan-stop imp | p+ implant | metal 1 etch |
| p-well drive | BF2 implant | Alloy |
| nitride strip | h-gate mask | Lift-off mask |
| threshold imp | h-gate implant split | Lift-off etch |
| gate ox | boe etchback | Cr dep |
| poly dep | h-gate oxidation 200A | NiPd dep |
| poly dope | R&D nitride dep 200A | Acetone lift-off |
| poly mask | nitride 2 mask | Anneal |
| poly etch | nitride dry etch | |

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the block diagrams.

The claims should not be read as limited to the described order or elements unless stated to that effect. In addition, use of the term "means" in any claim is intended to invoke 35 U.S.C. §112, paragraph 6, and any claim without the word "means" is not so intended. Therefore, all embodiments that come within the scope and spirit of the following claims and equivalents thereto are claimed as the invention.

Preferred and alternative embodiments of the present invention have been illustrated and described. It will be understood, however, that changes and modifications may be made to the invention without deviating from its true spirit and scope, as defined by the following claims.

What is claimed is:

1. A silicon-based hydrogen sensor having at least one hydrogen-exposed electrically-resistive hydrogen sense layer, wherein an adhesion-promoting layer is disposed between the hydrogen-exposed electrically-resistive hydrogen sense layer and an underlying base layer, and wherein a resistance associated with the hydrogen-exposed electrically-resistive hydrogen sense layer is indicative of a hydrogen concentration.

2. The sensor of claim 1, wherein the hydrogen sense-resistive layer includes a palladium nickel alloy.

3. The sensor of claim 1, wherein the adhesion-promoting layer includes chromium.

4. The sensor of claim 1, wherein the hydrogen sense-resistive layer is part of a hydrogen sense resistor.

5. The sensor of claim 1, comprising:
a sense transistor for determining hydrogen concentration within a first range;
a sense resistor for determining hydrogen concentration within a second range;
a temperature sensor for determining a sensor temperature; and
a temperature control module for controlling the temperature of the sensor.

6. The sensor of claim 5, wherein the sense transistor is a palladium-nickel-gate sense transistor, wherein the sense resistor is a palladium-nickel sense resistor, wherein the adhesion-promoting layer is a chromium thin film, and wherein the adhesion-promoting layer and the hydrogen sense-resistive layer form a first layer comprising chromium and palladium-nickel.

7. The sensor of claim 6, wherein the chromium thin film is approximately fifty (50) Angstroms thick.

8. The sensor of claim 6, wherein the first layer is patterned by a lift-off process.

9. The sensor of claim 6, wherein the hydrogen sense-resistive layer and the adhesion-promoting layer are deposited by a plating process.

10. A method for fabricating a silicon-based hydrogen sensor, comprising in combination:
depositing an adhesion-promoting layer on a base layer; and
depositing an electrically resistive hydrogen sense layer onto the adhesion-promoting layer, wherein the sense layer includes a surface exposed to an atmosphere surrounding the sensor and wherein said sensor comprises at least one sense transistor and at least one sense resistor.

11. The method of claim 10, wherein the silicon-based hydrogen sensor is a single chip sensor comprising a bulk silicon substrate and temperature control means.

12. The method of claim 10, wherein the adhesion-promoting layer is a thin film layer comprising chromium, and wherein the sense-resistive layer is a thin film layer comprising palladium nickel.

13. The method of claim 11, wherein the adhesion-promoting layer is a thin film layer comprising chromium, and wherein the sense-resistive layer is a thin film layer comprising palladium nickel.

14. The method of claim 13, further comprising:
patterning a layer of photoresist over the base layer prior to depositing the adhesion-promoting layer and the sense-resistive layer; and
removing the patterned layer of photoresist to expose a desired structure for the sense resistor.

15. A method for fabricating a single-chip hydrogen sensing-device, comprising in combination:
coating a photoresist layer over a base layer of the device;
removing a first pattern from the photoresist layer, wherein the first pattern corresponds to a desired layout of the sense resistor;

depositing a layer of chromium over the base layer and the patterned photoresist layer;

depositing a layer of palladium nickel over the layer of chromium; and removing a second pattern from the photoresist layer to lift off a portion of the chromium and palladium nickel layers not corresponding to the desired layout of the sense resistor.

16. The method of claim 15, wherein first pattern is removed by applying light energy to the pattern and dissolving the pattern as exposed by the light energy.

17. The method of claim 15, wherein the second pattern is removed in a lift-off process.

18. The method of claim 15, wherein the base layer includes at least one component selected from the group consisting of a semiconductor substrate, a conductive layer, a semiconductor layer, and a non-conductive layer.

19. The method of claim 15, wherein the chromium and palladium nickel films are deposited by a plating process.

* * * * *

UNITED STATES PATENT AND TRADEMARK OFFICE
CERTIFICATE OF CORRECTION

PATENT NO.    : 6,450,007 B1
DATED         : September 17, 2002
INVENTOR(S)   : O'Connor It is certified that error appears in the above-identified patent and that said Letters Patent is hereby corrected as shown below:

Title page,
Item [57], ABSTRACT,
Line 9, after the word "sensor", please insert -- without using any compensation by a hydrogen-isolated reference layer --

Column 8,
Line 4, after the word "concentration", please add -- without compensation by a hydrogen-isolated reference layer --
Line 43, after the word "resistor", please add -- to sense hydrogen concentration without a compensating hydrogen-isolated reference layer --

Signed and Sealed this

Twenty-fourth Day of August, 2004

JON W. DUDAS
*Director of the United States Patent and Trademark Office*